US009226675B2

(12) United States Patent
Tao et al.

(10) Patent No.: US 9,226,675 B2
(45) Date of Patent: Jan. 5, 2016

(54) ELECTROCARDIOGRAPHY MEASUREMENT METHOD AND AN ELECTROCARDIOGRAPHY MEASUREMENT DEVICE APPLYING THE SAME

(71) Applicant: Wistron Corporation, New Taipei (TW)

(72) Inventors: Yi-Wei Tao, New Taipei (TW); Wen-Hui Shih, New Taipei (TW)

(73) Assignee: WISTRON CORPORATION, New Taipei (TW)

( * ) Notice: Subject to any disclaimer, the term of this patent is extended or adjusted under 35 U.S.C. 154(b) by 35 days.

(21) Appl. No.: 14/444,602

(22) Filed: Jul. 28, 2014

(65) Prior Publication Data

US 2015/0190069 A1    Jul. 9, 2015

(30) Foreign Application Priority Data

Jan. 3, 2014   (TW) .............. 103100191 A

(51) Int. Cl.
*A61B 5/04* (2006.01)
*A61B 5/0402* (2006.01)

(52) U.S. Cl.
CPC ........... *A61B 5/04012* (2013.01); *A61B 5/0402* (2013.01)

(58) Field of Classification Search
None
See application file for complete search history.

(56) References Cited

U.S. PATENT DOCUMENTS

| | | | | |
|---|---|---|---|---|
| 3,885,552 A | * | 5/1975 | Kennedy | A61B 5/0006 128/904 |
| 8,112,147 B2 | * | 2/2012 | Ye | A61B 5/0472 600/509 |
| 8,209,000 B2 | | 6/2012 | Kuo et al. | |
| 8,568,329 B2 | * | 10/2013 | Lee | A61B 5/0402 600/508 |
| 2014/0058280 A1 | * | 2/2014 | Chefles | A61B 5/0006 600/521 |

* cited by examiner

*Primary Examiner* — Brian T Gedeon
(74) *Attorney, Agent, or Firm* — Kirton McConkie; Evan R. Witt

(57) ABSTRACT

In an electrocardiography measurement method and device, a signal processor determines a baseline value, a maximum wave amplitude value, and a minimum wave amplitude value in an electrocardiogram signal. When the signal processor determines that a difference of the maximum wave amplitude value minus the baseline value is less than a difference of the baseline value minus the minimum wave amplitude value, the signal processor performs a correction process for correcting the electrocardiogram signal.

19 Claims, 5 Drawing Sheets

ELECTROCARDIOGRAPHY MEASUREMENT METHOD AND AN ELECTROCARDIOGRAPHY MEASUREMENT DEVICE APPLYING THE SAME

CROSS-REFERENCE TO RELATED APPLICATION

This application claims priority of Taiwanese application no. 103100191, filed on Jan. 3, 2014, the entire disclose of which is incorporated herein by reference.

BACKGROUND OF THE INVENTION

1. Field of the Invention

The present invention relates to an electrocardiography measurement method and an electrocardiography measurement device applying the same.

2. Description of the Related Art

FIG. 1 shows a conventional basic portable card-type electrocardiography measurement device 1. For user convenience, this type of measurement device uses 1-Lead electrocardiography for reading a cardio electrical signal of a subject, i.e., the subject's right and left hands respectively contact (press on) first and second electrodes 11, 12 of the electrocardiography measurement device 1 for obtaining an electrocardiogram of the subject. By design, the right hand has to contact the first electrode 11, and the left hand has to contact the second electrode 12. If the right and left hands contact the first electrode 11 and the second electrode 12 in a reversed manner (electrode inversion), the electrocardiography measurement device 1 will output an inverse electrocardiogram, which affects a reading on the electrocardiogram. However, not every subject is always careful enough to contact the first and second electrodes 11, 12 correctly.

Therefore, if an electrocardiography measurement device is able to automatically detect for electrode inversion and perform a correction process for obtaining a correct electrocardiogram, it would be more convenient for the subject using the electrocardiography measurement device.

SUMMARY OF THE INVENTION

The object of the present invention is to provide an electrocardiography measurement method to be implemented using an electrocardiography measurement device that can automatically perform a correction process for correcting an electrocardiogram signal.

According to one aspect of the present invention, there is provided an electrocardiography measurement method for an electrocardiography measurement device. The electrocardiography measurement device includes a first electrode and a second electrode to be brought into contact with a right hand and a left hand of a subject respectively for reading a cardio electrical signal of the subject, a signal amplifier electrically coupled with the first electrode and the second electrode and operable to amplify the cardio electrical signal and to generate an electrocardiogram signal based on the cardio electrical signal, and a signal processor electrically coupled with the signal amplifier for receiving the electrocardiogram signal.

The electrocardiography measurement method comprises the steps of:

(A) determining, using the signal processor, a baseline value, a maximum wave amplitude value, and a minimum wave amplitude value in the electrocardiogram signal;

(B) when the signal processor determines that a difference of the maximum wave amplitude value minus the baseline value is greater than a difference of the baseline value minus the minimum wave amplitude value, acquiring, using the signal processor, the electrocardiogram signal; and (C) when the signal processor determines that the difference of the maximum wave amplitude value minus the baseline value is less than the difference of the baseline value minus the minimum wave amplitude value, performing, using the signal processor, a correction process for correcting the electrocardiogram signal.

Another object of the present invention is to provide an electrocardiography measurement device that applies the electrocardiography measurement method of this invention.

According to another aspect of the present invention, an electrocardiography measurement device comprises:

a first electrode and a second electrode configured to be brought into contact with a right hand and a left hand of a subject respectively for reading a cardio electrical signal of the subject;

a signal amplifier electrically coupled with the first electrode and the second electrode for amplifying the cardio electrical signal to generate an electrocardiogram signal; and a signal processor electrically coupled with the signal amplifier for receiving the electrocardiogram signal.

The signal processor is configured to determine a baseline value, a maximum wave amplitude value, and a minimum wave amplitude value in the electrocardiogram signal.

When the signal processor determines that a difference of the maximum wave amplitude value minus the baseline value is greater than a difference of the baseline value minus the minimum wave amplitude value, the signal processor is configured to acquire the electrocardiogram signal.

When the signal processor determines that the difference of the maximum wave amplitude value minus the baseline value is less than the difference of the baseline value minus the minimum wave amplitude value, the signal processor is configured to perform a correction process for correcting the electrocardiogram signal.

BRIEF DESCRIPTION OF THE DRAWINGS

Other features and advantages of the present invention will become apparent in the following detailed description of the embodiments with reference to the accompanying drawings, of which.

DETAILED DESCRIPTION OF THE EMBODIMENTS

Figure 1:
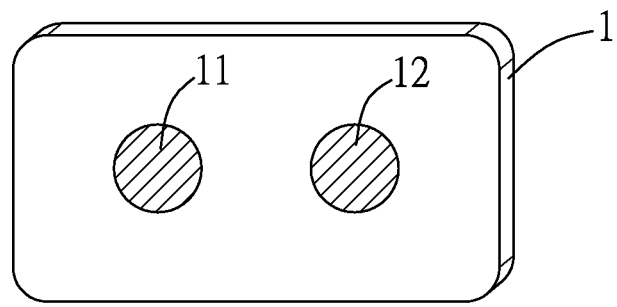
FIG. 1 is a schematic diagram illustrating a conventional card-type electrocardiography measurement device.
Figure 2:
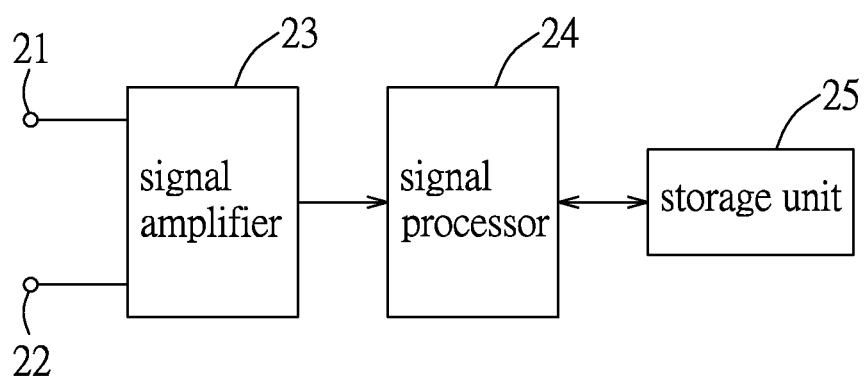
FIG. 2 is a circuit block diagram of an electrocardiography measurement device of a first embodiment of the present invention.

FIG. 2 shows a first embodiment of an electrocardiography measurement device that includes a first electrode 21, a second electrode 22, a signal amplifier 23 electrically coupled with the first electrode 21 and the second electrode 22, a signal processor 24 electrically coupled with the signal amplifier 23, and a storage unit 25 electrically coupled with the signal processor 24.

The electrocardiography measurement device utilizes Lead-1 process for reading a cardio electrical signal, i.e., the first electrode 21 and the second electrode 22 are brought into contact with a finger of a right hand and a finger of a left hand of a subject respectively for reading a cardio electrical signal of the subject through the right and left hands.

Figure 3:
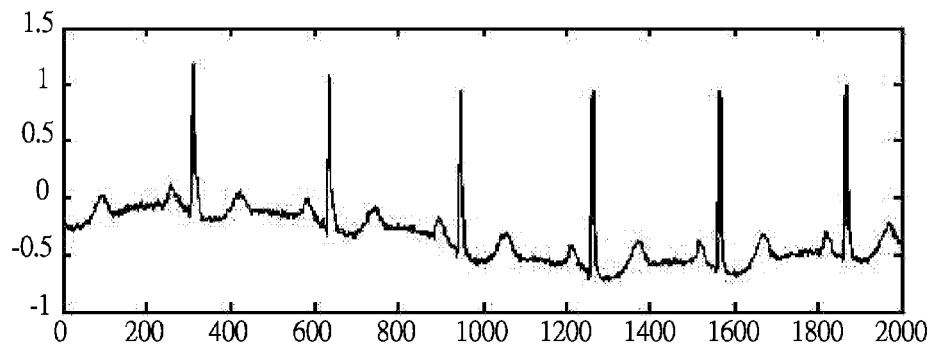
FIG. 3 is a graph illustrating a waveform of an electrocardiogram signal.
Figure 4:
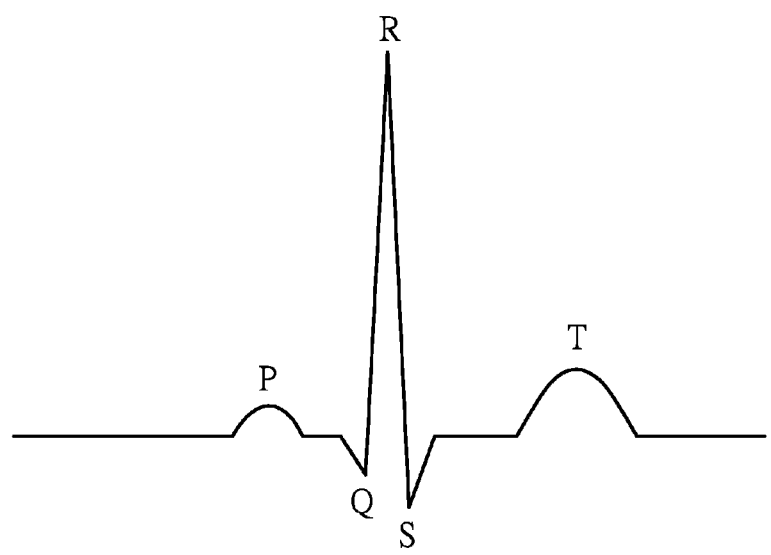
FIG. 4 is a graph illustrating a magnification of a section of the waveform of the electrocardiogram signal.

When the first electrode 21 and the second electrode 22 are contacted by the subject correctly, i.e., with the finger of the right hand contacting the first electrode 21 (a positive terminal) and with the finger of the left hand contacting the second electrode 22 (a negative terminal), the signal amplifier 23 amplifies the cardio electrical signal to generate an electrocardiogram signal as shown in FIG. 3. FIG. 4 shows a magnification of the electrocardiogram signal, and the magnification shows a maximum wave amplitude value (R wave amplitude value) that is significantly larger than a minimum wave amplitude value (S wave amplitude value) related to a PQRST waveform.

Figure 5:
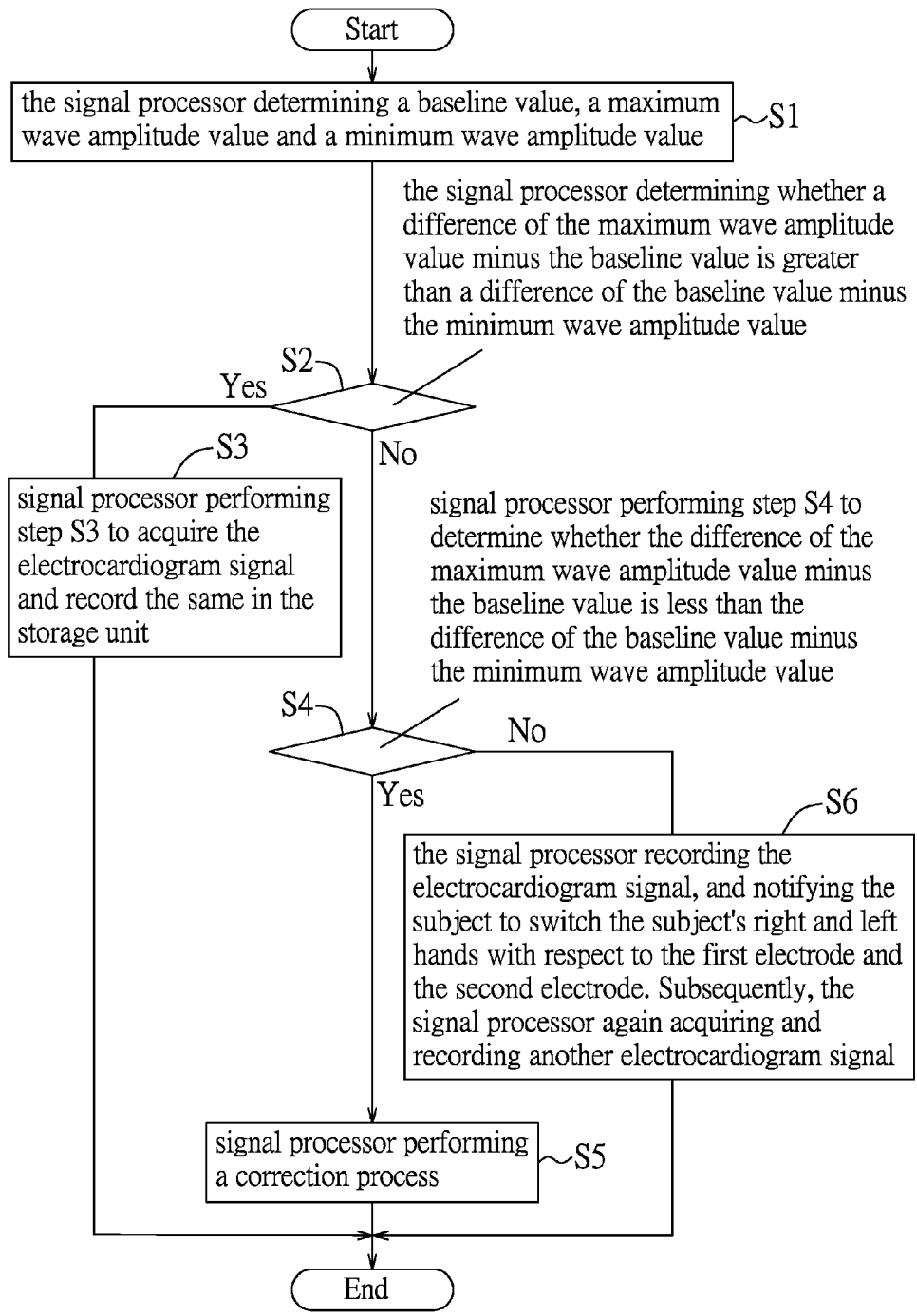
FIG. 5 is a flow chart illustrating an embodiment of an electrocardiography measurement method of the present invention.

The signal processor 24 receives the electrocardiogram signal from the signal amplifier 23, and in order to determine whether the electrocardiogram signal is measured correctly by having the finger of the right hand of the subject contacting the first electrode 21 (positive terminal) and the finger of the left hand of the subject contacting the second electrode (negative terminal), the signal processor 24 is configured to automatically perform an electrocardiography measurement method, as shown in FIG. 5.

Figure 6:
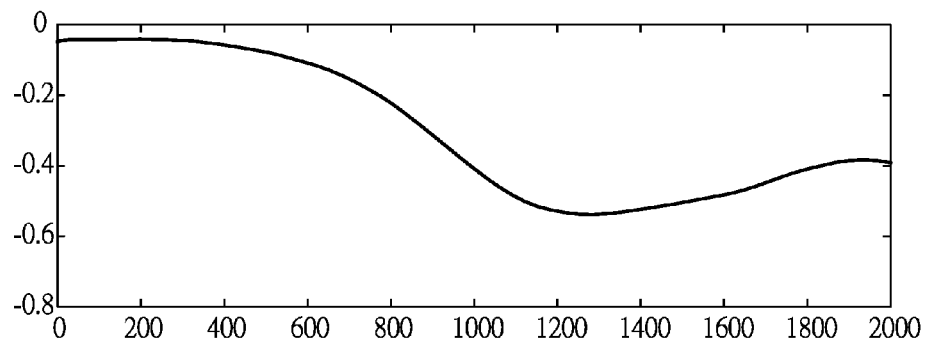
FIG. 6 is a graph illustrating a baseline value waveform based on the electrocardiogram signal of FIG. 3.

As shown in FIG. 5, in step S1, the signal processor 24 determines a baseline value (as shown in FIG. 6), a maximum wave amplitude value (R wave amplitude value as shown in FIG. 4) and a minimum wave amplitude value (S wave amplitude value as shown in FIG. 4) in the electrocardiogram signal. In this embodiment, the signal processor 24 determines the baseline value, the maximum wave amplitude value, and the minimum wave amplitude value using Hilbert-Huang Transform (HHT) based on empirical mode decomposition (EMD). However, other signal decomposition methods may be applied to obtain the baseline value, the maximum wave amplitude value, and the minimum wave amplitude value.

In step S2, the signal processor 24 determines whether a difference of the maximum wave amplitude value minus the baseline value is greater than a difference of the baseline value minus the minimum wave amplitude value.

If yes, the signal processor 24 performs step S3 to acquire the electrocardiogram signal and record the same in the storage unit 25, ending the electrocardiography measurement method, since the electrocardiogram signal is non-inverted in which the maximum wave amplitude value is far greater than the minimum wave amplitude value, and the first electrode 21 and the second electrode 22 are being contacted with the correct hands of the subject.

On the other hand, if no, the signal processor 24 performs step S4 in FIG. 5, to determine whether the difference of the maximum wave amplitude value minus the baseline value is less than the difference of the baseline value minus the minimum wave amplitude value. If yes, the signal processor 24 performs, in step S5, a correction process for correcting the electrocardiogram signal, since the electrocardiogram signal is inverted (rotated 180 degrees) in which the minimum wave amplitude value is far greater than the maximum wave amplitude value, and the first electrode 21 and the second electrode 22 are being contacted with the wrong hands of the subject, i.e., the right hand of the subject is contacting the second electrode 22 (negative electrode) and the left hand of the subject is contacting the first electrode 21 (positive electrode).

In this embodiment, the signal processor 24 performs the correction process by inversion processing of the electrocardiogram signal using a software (inverting the electrocardiogram signal that is inverted), and recording the electrocardiogram signal thus inverted in the storage unit 25, ending the electrocardiography measurement method.

Figure 7:
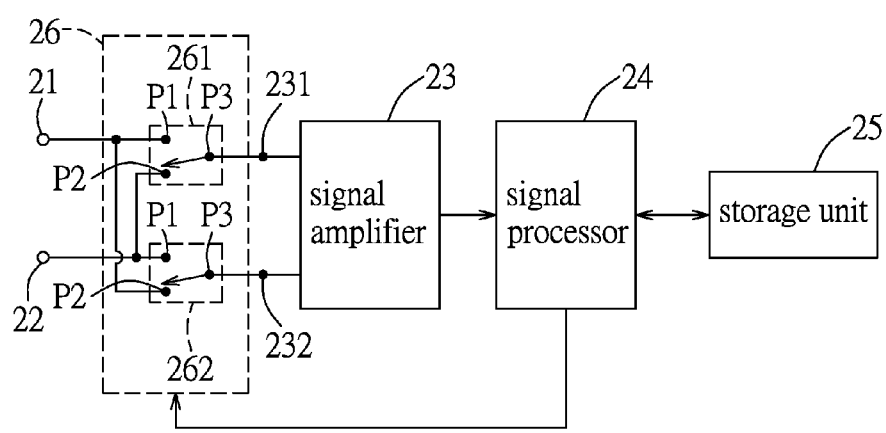
FIG. 7 is a circuit block diagram of a second embodiment of the electrocardiography measurement device of the present invention.

FIG. 7 shows a second embodiment of the electrocardiography measurement device that is different from the first embodiment in that the second embodiment further includes a switching unit 26 connected electrically to the first electrode 21 and the second electrode 22. Prior to the signal processor 24 determining a baseline value, a maximum wave amplitude value, and a minimum wave amplitude value in the electrocardiogram signal, the signal processor 24 controls the switching unit 26 to electrically connect the first electrode 21 with a first input terminal 231 of the signal amplifier 23 and to electrically connect the second electrode 22 with a second input terminal 232 of the signal amplifier 23.

In step S5 of the electrocardiography measurement method, the signal processor 24 performs the correction process by controlling the switching unit 26 to switch the first electrode 21 to be electrically connected with the second input terminal 232 of the signal amplifier and to switch the second electrode 22 to be electrically connected with the first input terminal 231 of the signal amplifier 23, and the signal processor 24 then acquires and records the electrocardiogram signal generated by the signal amplifier 23. By such virtue, in case the electrocardiogram signal is inverted due to a situation where the first electrode 21 and the second electrode 22 are being contacted with the wrong hands of the subject, i.e., the right hand of the subject is contacting the second electrode 22 (negative electrode) and the left hand of the subject is contacting the first electrode 21 (positive electrode), the signal processor 24 is able to perform the correction process to enable the signal amplifier 23 to receive the electrocardiogram signal that is not inverted.

More specifically, the switching unit 26 includes a first switch 261 and a second switch 262. The first switch 261 has a first input contact P1, a second input contact P2, and a first output contact P3 electrically coupled with the first input terminal 231 of the signal amplifier 23. The second switch 262 has a third input contact P1, a fourth input contact P2, and a second output contact P3 electrically coupled with the second input terminal 232 of the signal amplifier 23. Furthermore, the first electrode 21 is electrically coupled with the first input contact P1 of the first switch 261 and with the fourth input contact P2 of the second switch 262, and the second electrode 22 is electrically coupled with the second input contact P2 of the first switch 261 and with the third input contact P1 of the second switch 262.

When the signal processor 24 is not performing the correction process, i.e., the first electrode 21 and the second electrode 22 are being contacted by the right hand and the left hand of the subject, respectively, the signal processor 24 is configured to control the switching unit 26 to electrically connect the first output contact P3 of the first switch 261 and the second output contact P3 of the second switch 262 with the first input contact P1 of the first switch 261 and the third input contact P1 of the second switch 262, respectively.

On the other hand, when the signal processor 24 is performing the correction process, i.e., the first electrode 21 and the second electrode 22 are being contacted by the left hand and the right hand of the subject, respectively, the signal processor 24 is configured to control the switching unit 26 to electrically connect the first output contact P3 of the first switch 261 and the second output contact P3 of the second switch 262 with the second input contact P2 of the first switch 261 and the fourth input contact P2 of the second switch 262, respectively, such that the first electrode 21 is electrically connected with the second input terminal 232 of the signal amplifier 23 and the second electrode 22 is electrically connected with the first input terminal 231 of the signal amplifier 23. This enables the signal amplifier 23 to receive a correct input of the cardio electrical signal.

Figure 8:
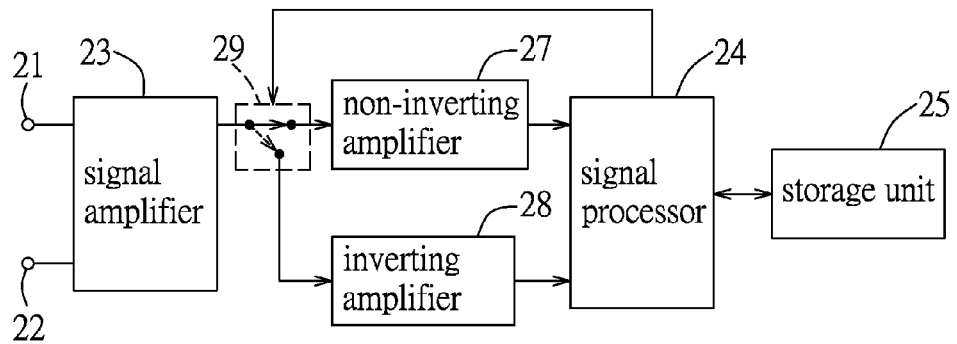
FIG. 8 is a circuit block diagram of a third embodiment of the electrocardiography measurement device of the present invention.

FIG. 8 shows a third embodiment of the electrocardiography measurement device that is different from the first embodiment in that the third embodiment further includes a non-inverting amplifier 27 and an inverting amplifier 28 each electrically coupled between the signal amplifier 23 and the signal processor 24, and a third switch 29 that is electrically coupled between the signal amplifier 23, the non-inverting amplifier 27 and the inverting amplifier 28 and that is controlled by the signal processor 24. The non-inverting amplifier 27 and the inverting amplifier 28 each has an output terminal that is electrically connected with the signal processor 24.

When the signal processor 24 is not performing the correction process, i.e., the first electrode 21 and the second electrode 22 are being contacted by the right hand and the left hand of the subject, respectively, the signal processor 24 controls the third switch 29 to make connection between the signal amplifier 23 and the non-inverting amplifier 27, such that the electrocardiogram signal is transmitted through the non-inverting amplifier 27 to the signal processor 24. On the other hand, when the signal processor 24 is performing the correction process, the signal processor 24 controls the third switch 29 to make connection between the signal amplifier 23 and the inverting amplifier 28, such that the electrocardiogram signal is transmitted through the inverting amplifier 28 to the signal processor 24. By such virtue, in case the electrocardiogram signal is inverted due to a situation where the first electrode 21 and the second electrode 22 are being contacted with the wrong hands of the subject, the electrocardiogram signal that is inverted can be corrected by the inverting amplifier 28, which is then recorded in the storage unit 25.

Alternatively, the third switch 29 can be built in or integrated into the signal amplifier 23, and controlled by the signal processor 24 to electrically connect the signal amplifier 23 with the non-inverting amplifier 27 or the inverting amplifier 28.

Figure 9:
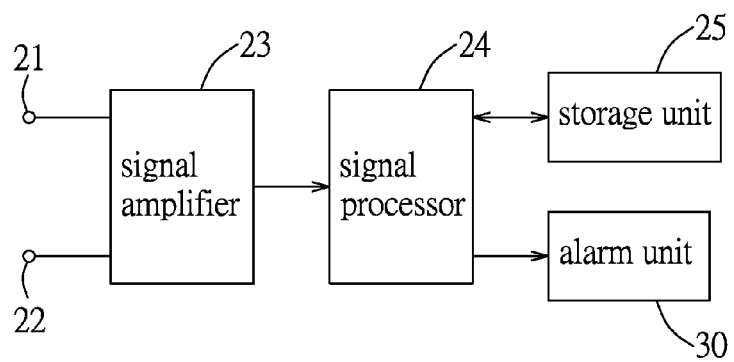
FIG. 9 is a circuit block diagram of a fourth embodiment of the electrocardiography measurement device of the present invention.

FIG. 9 shows a fourth embodiment of the electrocardiography measurement device that is different from the first embodiment in that the fourth embodiment further includes an alarm unit 30 electrically coupled with the signal processor 24. The alarm unit 30 may be, for instance, a warning light or a buzzer.

When the signal processor 24 is performing the correction process, i.e., the first electrode 21 and the second electrode 22 are being contacted by the left hand and the right hand of the subject, respectively, the signal processor 24 controls the alarm unit 30 to output an alarm notification, such as a flashing of light by the warning light or buzzing by the buzzer, to remind someone that the first electrode 21 and the second electrode 22 are contacted in a reversed manner.

In step S4 of the electrocardiography measurement method, if the signal processor 24 determines that the difference of the maximum wave amplitude value minus the baseline value is not less than the difference of the baseline value minus the minimum wave amplitude value, this implies that the signal processor 24 is unable to recognize the electrocardiogram signal as being non-inverted or inverted. In this case, the signal processor 24 will perform step S6, in which the signal processor 24 records the electrocardiogram signal, and may notify the subject via the alarm unit 30 to switch the subject's right and left hands with respect to the first electrode 21 and the second electrode 22. Subsequently, the signal processor 24 again acquires and records another electrocardiogram signal, such that a person can interpret on both electrocardiogram signals.

In summary, in the above-mentioned embodiments, the signal processor 24 determines, based on the baseline value, the maximum wave amplitude value, and the minimum wave amplitude value in an electrocardiogram signal, whether or not the electrocardiogram signal is inverted, and automatically performs the correction process for correcting the electrocardiogram signal that is inverted and may at the same time output an alarm notification, such that the electrocardiogram signal recorded by the electrocardiography measurement device is correct. By this virtue, greater convenience is provided for users of the electrocardiography measurement device.

While the present invention has been described in connection with what are considered the most practical and embodiments, it is understood that this invention is not limited to the disclosed embodiments but is intended to cover various arrangements included within the spirit and scope of the broadest interpretation so as to encompass all such modifications and equivalent arrangements.

What is claimed is:

1. An electrocardiography measurement method to be implemented using an electrocardiography measurement device, the electrocardiography measurement device including a first electrode and a second electrode to be brought into contact with a right hand and a left hand of a subject respectively for reading a cardio electrical signal of the subject, a signal amplifier electrically coupled with the first electrode and the second electrode and operable to amplify the cardio electrical signal and to generate an electrocardiogram signal based on the cardio electrical signal, and a signal processor electrically coupled with the signal amplifier for receiving the electrocardiogram signal, the electrocardiography measurement method comprising the steps of:

(A) determining, using the signal processor, a baseline value, a maximum wave amplitude value, and a minimum wave amplitude value in the electrocardiogram signal;

(B) when the signal processor determines that a difference of the maximum wave amplitude value minus the baseline value is greater than a difference of the baseline value minus the minimum wave amplitude value, acquiring, using the signal processor, the electrocardiogram signal; and (C) when the signal processor determines that the difference of the maximum wave amplitude value minus the baseline value is less than the difference of the baseline value minus the minimum wave amplitude value, performing, using the signal processor, a correction process for correcting the electrocardiogram signal.

2. The electrocardiography measurement method as claimed in claim 1, wherein, in step (A), the signal processor determines the baseline value, the maximum wave amplitude value, and the minimum wave amplitude value using empirical mode decomposition.

3. The electrocardiography measurement method as claimed in claim 1, the signal amplifier having a first input terminal and a second input terminal, the electrocardiography measurement device further including a switching unit connected electrically to the first electrode, the second electrode, the first input terminal and the second input terminal, wherein:
prior to step (A), the signal processor controls the switching unit to electrically connect the first electrode with the first input terminal of the signal amplifier and to electrically connect the second electrode with the second input terminal of the signal amplifier; and
instep (C), the correction process performed using the signal processor includes controlling the switching unit to switch the first electrode to be electrically connected with the second input terminal of the signal amplifier and to switch the second electrode to be electrically connected with the first input terminal of the signal amplifier.

4. The electrocardiography measurement method as claimed in claim 1, the electrocardiography measurement device further including a first amplifier and a second amplifier each electrically coupled between the signal amplifier and the signal processor, one of the first amplifier and the second amplifier being a non-inverting amplifier, the other one of the first amplifier and the second amplifier being an inverting amplifier, wherein:
prior to step (A), the signal processor performs control to make connection between the signal amplifier and the first amplifier and to break connection between the signal amplifier and the second amplifier, such that the electrocardiogram signal is transmitted through the first amplifier to the signal processor; and
in step (C), the correction process performed using the signal processor includes performing control to make connection between the signal amplifier and the second amplifier and to break connection between the signal amplifier and the first amplifier, such that the electrocardiogram signal is transmitted through the second amplifier to the signal processor.

5. The electrocardiography measurement method as claimed in claim 1, wherein, in step (C), the correction process performed using the signal processor includes inversion processing of the electrocardiogram signal, and recording the electrocardiogram signal thus inverted.

6. The electrocardiography measurement method as claimed in claim 1, the electrocardiography measurement device further including an alarm unit electrically coupled with the signal processor, wherein step (C) further includes controlling, using the signal processor, the alarm unit to output an alarm notification when the signal processor performs the correction process.

7. The electrocardiography measurement method as claimed in claim 1, wherein the maximum wave amplitude value and the minimum wave amplitude value are a R wave amplitude value and a S wave amplitude value related to a PQRST waveform in the electrocardiogram signal.

8. The electrocardiography measurement method as claimed in claim 2, wherein the maximum wave amplitude value and the minimum wave amplitude value are a R wave amplitude value and a S wave amplitude value related to a PQRST waveform in the electrocardiogram signal.

9. An electrocardiography measurement device comprising:
a first electrode and a second electrode configured to be brought into contact with a right hand and a left hand of a subject respectively for reading a cardio electrical signal of the subject;
a signal amplifier electrically coupled with the first electrode and the second electrode for amplifying the cardio electrical signal to generate an electrocardiogram signal; and
a signal processor electrically coupled with the signal amplifier for receiving the electrocardiogram signal;
wherein:
the signal processor is configured to determine a baseline value, a maximum wave amplitude value, and a minimum wave amplitude value in the electrocardiogram signal;
when the signal processor determines that a difference of the maximum wave amplitude value minus the baseline value is greater than a difference of the baseline value minus the minimum wave amplitude value, the signal processor is configured to acquire the electrocardiogram signal; and
when the signal processor determines that the difference of the maximum wave amplitude value minus the baseline value is less than the difference of the baseline value minus the minimum wave amplitude value, the signal processor is configured to perform a correction process for correcting the electrocardiogram signal.

10. The electrocardiography measurement device as claimed in claim 9, wherein the signal processor is configured to determine the baseline value, the maximum wave amplitude value and the minimum wave amplitude value using empirical mode decomposition.

11. The electrocardiography measurement device as claimed in claim 9, wherein:
the signal amplifier has a first input terminal and a second input terminal;
the electrocardiography measurement device further comprises a switching unit connected electrically to the first electrode, the second electrode, the first input terminal and the second input terminal;
prior to determining the baseline value, the maximum wave amplitude value and the minimum wave amplitude value, the signal processor is configured to control the switching unit to electrically connect the first electrode with the first input terminal of the signal amplifier and to electrically connect the second electrode with the second input terminal of the signal amplifier; and
the correction process performed by the signal processor includes controlling the switching unit to switch the first electrode to be electrically connected with the second input terminal of the signal amplifier and to switch the second electrode to be electrically connected with the first input terminal of the signal amplifier.

12. The electrocardiography measurement device as claimed in claim 11, wherein:
the switching unit includes a first switch and a second switch, the first switch having a first input contact, a second input contact, and a first output contact electrically coupled with the first input terminal of the signal amplifier, the second switch having a third input contact, a fourth input contact, and a second output contact electrically coupled with the second input terminal of the signal amplifier;

one of the first electrode and the second electrode is electrically coupled with the first input contact of the first switch and with the fourth input contact of the second switch; and the other one of the first electrode and the second electrode is electrically coupled with the second input contact of the first switch and with the third input contact of the second switch.

13. The electrocardiography measurement device as claimed in claim 12, wherein:

when the signal processor is not performing the correction process, the signal processor is configured to control the switching unit to electrically connect the first output contact and the second output contact with the first input contact and the third input contact, respectively; and when the signal processor is performing the correction process, the signal processor is configured to control the switching unit to electrically connect the first output contact and the second output contact with the second input contact and the fourth input contact, respectively.

14. The electrocardiography measurement device as claimed in claim 9, further comprising:

a first amplifier and a second amplifier each electrically coupled between the signal amplifier and the signal processor, one of the first amplifier and the second amplifier being a non-inverting amplifier, the other one of the first amplifier and the second amplifier being an inverting amplifier, wherein:

prior to determining the baseline value, the maximum wave amplitude value and the minimum wave amplitude value, the signal processor is configured to perform control to make connection between the signal amplifier and the first amplifier and to break connection between the signal amplifier and the second amplifier, such that the electrocardiogram signal is transmitted through the first amplifier to the signal processor; and when the signal processor performs the correction process, the signal processor is configured to perform control to make connection between the signal amplifier and the second amplifier and to break connection between the signal amplifier and the first amplifier, such that the electrocardiogram signal is transmitted through the second amplifier to the signal processor.

15. The electrocardiography measurement device as claimed in claim 9, wherein the correction process performed by the signal processor includes inversion processing of the electrocardiogram signal, and recording the electrocardiogram signal thus inverted.

16. The electrocardiography measurement device as claimed in claim 9, further comprising an alarm unit electrically coupled with and controlled by the signal processor to output an alarm notification when the signal processor performs the correction process.

17. The electrocardiography measurement device as claimed in claim 9, further comprising a storage unit electrically coupled with the signal processor for recording of the electrocardiogram signal.

18. The electrocardiography measurement device as claimed in claim 9, wherein the maximum amplitude value and the minimum amplitude value are a R wave amplitude value and a S wave amplitude value related to a PQRST waveform in the electrocardiogram signal.

19. The electrocardiography measurement device as claimed in claim 10, wherein the maximum amplitude value and the minimum amplitude value are a R wave amplitude value and a S wave amplitude value related to a PQRST waveform in the electrocardiogram signal.

* * * * *